(12) United States Patent
Furnish et al.

(10) Patent No.: US 7,873,406 B2
(45) Date of Patent: Jan. 18, 2011

(54) SPECTROSCOPE FOR RECOVERING LIGHT FROM RE-ENTRANT ZONE OF ARTERIAL WALL

(75) Inventors: Simon Furnish, New York, NY (US); Andres Zuluaga, Boston, MA (US)

(73) Assignee: InfraReDx, Inc., Burlington, MA (US)

( * ) Notice: Subject to any disclaimer, the term of this patent is extended or adjusted under 35 U.S.C. 154(b) by 490 days.

(21) Appl. No.: 11/772,887

(22) Filed: Jul. 3, 2007

(65) Prior Publication Data

US 2007/0255142 A1 Nov. 1, 2007

Related U.S. Application Data

(62) Division of application No. 10/289,741, filed on Nov. 7, 2002, now abandoned.

(51) Int. Cl.
*A61B 6/00* (2006.01)
(52) U.S. Cl. ........................ 600/473; 600/475
(58) Field of Classification Search ......... 600/309–344, 600/473–480, 407, 408; 606/1–19
See application file for complete search history.

(56) References Cited

U.S. PATENT DOCUMENTS

| | | | |
|---|---|---|---|
| 4,573,761 A | 3/1986 | McLachlan et al. | |
| 4,705,354 A | 11/1987 | Ulrich | |
| 4,768,513 A | 9/1988 | Suzuki | |
| 4,768,873 A | 9/1988 | Webb | |
| 4,838,643 A | 6/1989 | Hodges et al. | |
| 4,896,941 A | 1/1990 | Hayashi et al. | |
| 4,921,326 A | 5/1990 | Wild et al. | |
| 4,991,947 A | 2/1991 | Sander et al. | |
| 5,057,695 A | 10/1991 | Hirao et al. | |
| 5,106,387 A | 4/1992 | Kittrell et al. | |
| 5,127,079 A | 6/1992 | Suzuki et al. | |
| 5,261,904 A | 11/1993 | Baker et al. | |
| 5,318,024 A * | 6/1994 | Kittrell et al. | 600/478 |
| 5,418,880 A | 5/1995 | Lewis et al. | |
| 5,452,723 A | 9/1995 | Wu et al. | |
| 5,537,499 A | 7/1996 | Brekke | |
| 5,551,422 A | 9/1996 | Simonsen et al. | |
| 5,566,196 A | 10/1996 | Scifres | |
| 5,636,633 A | 6/1997 | Messerschmidt et al. | |
| 5,713,364 A | 2/1998 | DeBaryshe et al. | |
| 5,764,840 A | 6/1998 | Wach | |
| 5,813,987 A * | 9/1998 | Modell et al. | 600/473 |

(Continued)

FOREIGN PATENT DOCUMENTS

WO WO00/13578 3/2000

OTHER PUBLICATIONS

Barber et al., "Ultrasonic Duplex Echo-Doppler Scanner," *IEEE Transactions on Biomedical Engineering*, vol. BME-21, No. 2, pp. 109-113 (Mar. 1974).

(Continued)

*Primary Examiner*—Brian Casler
*Assistant Examiner*—Elmer Chao
(74) *Attorney, Agent, or Firm*—Rothwell, Figg, Ernst & Manbeck, P.C.

(57) ABSTRACT

A spectroscope includes an optical fiber extending through a catheter, and in communication with an optical system. The optical system has a finite focal length.

29 Claims, 11 Drawing Sheets

U.S. PATENT DOCUMENTS

| | | | |
|---|---|---|---|
| 5,838,860 | A | 11/1998 | Kingstone et al. |
| 5,878,178 | A | 3/1999 | Wach |
| 5,880,880 | A | 3/1999 | Anderson et al. |
| 5,901,261 | A | 5/1999 | Wach |
| 5,911,017 | A | 6/1999 | Wach et al. |
| 5,926,592 | A | 7/1999 | Harris et al. |
| 5,953,477 | A | 9/1999 | Wach et al. |
| 5,973,828 | A | 10/1999 | Webb |
| 5,995,283 | A | 11/1999 | Anderson et al. |
| 6,014,204 | A | 1/2000 | Prahl et al. |
| 6,081,371 | A | 6/2000 | Shioda et al. |
| 6,118,580 | A | 9/2000 | Webb |
| 6,121,603 | A | 9/2000 | Hang et al. |
| 6,144,791 | A * | 11/2000 | Wach et al. ............ 385/123 |
| 6,151,428 | A | 11/2000 | Vahala et al. |
| 6,157,763 | A | 12/2000 | Grubb et al. |
| 6,564,087 | B1 | 5/2003 | Pitris et al. |
| 6,564,088 | B1 | 5/2003 | Soller et al. |
| 6,643,065 | B1 * | 11/2003 | Silberman ............... 359/573 |
| 6,654,630 | B2 * | 11/2003 | Zuluaga et al. .......... 600/476 |
| 7,426,410 | B2 * | 9/2008 | Zuluaga et al. .......... 600/476 |
| 7,466,421 | B2 * | 12/2008 | Weitzel .................. 356/451 |

OTHER PUBLICATIONS

Bow et al., "Cardiac Imaging with a Real-Time Ultrasonic Scanner of a Rotating Transducer Design," *Proceedings of the British Medical Ultrasound Society*, p. 645 (Aug. 1978).

"Coronary-Artery Bypass Surgery," *The Lancet*, pp. 264-265 (Feb. 4, 1978).

Hisanaga et al., "High Speed Rotating Scanner for Transesophageal Cross-Sectional Echocardiography," *The American Journal of Cardiology*, vol. 46, pp. 837-842 (Nov. 1980).

Lancée et al., "Construction of a circular ultrasonic array with miniature elements for cardiac application." Thorax Center, Department of Echocardiography and Central Research Workshop, Erasmus University, Rotterdam, The Netherlands, pp. 49-53 (undated).

Martin et al., "An Ultrasonic Catheter Tip Instrument for Measuring Volume Blood Flow," Departments of Anesthesiology & Bioengineering, University of Washington, Seattle, Washington, pp. 13-17 (undated).

Martin et al., "Ultrasonic Catheter Tip Instrument for Measurement of Vessel, Cross-Sectional Area," $27^{th}$ ACEMB, Marriott Hotel, Philadelphia, Pennsylvania, p. 186 (Oct. 6-10, 1974).

Martin and Watkins, "An Ultrasonic Catheter for Intravascular Measurement of Blood Flow: Technical Details," *IEEE Transactions on Sonics and Ultrasonics*, vol. SU-27, No. 6, pp. 277-286 (Nov. 1980).

Pérez et al., "Applicability of Ultrasonic Tissue Characterization for Longitudinal Assessment and Differentiation of Calcification and Fibrosis in Cardiomyopathy," *American College of Cardiology*, vol. 4, No. 1, pp. 88-93 (Jul. 1984).

Tomoike et al., "Continuous measurement of coronary artery diameter in situ," *American Physiological Society*, pp. H73-H79 (undated).

Van Orden et al., "A technique for monitoring blood flow changes with miniaturized Doppler flow probes," *American Physiological Society*, pp. H1005-H1009 (undated).

Ycas and Barnes, "An Ultrasonic Drill for Cleaning Blood Vessels," Department of Electrical Engineering, University of Colorado, Boulder, Colorado, pp. 165-167 (undated).

Office Action dispatched Jan. 15, 2010 in related European patent application No. 03768797.7 (4pp.).

* cited by examiner

SPECTROSCOPE FOR RECOVERING LIGHT FROM RE-ENTRANT ZONE OF ARTERIAL WALL

RELATED APPLICATIONS

Pursuant to 35 USC 120, this application is a divisional application of, and claims the benefit of the priority date of U.S. patent application Ser. No. 10/289,741, filed Nov. 7, 2002, the contents of which are herein incorporated by reference.

FIELD OF INVENTION

The invention relates to spectroscopy, and in particular, to spectroscopes for detecting vulnerable plaques within a wall of a blood vessel.

BACKGROUND

Atherosclerosis is a vascular disease characterized by a modification of the walls of blood-carrying vessels. Such modifications, when they occur at discrete locations or pockets of diseased vessels, are referred to as plaques. Certain types of plaques are associated with acute events such as stroke or myocardial infarction. These plaques are referred to as "vulnerable plaques." A vulnerable plaque typically includes a lipid-containing pool of necrotic debris separated from the blood by a thin fibrous cap. In response to elevated intraluminal pressure or vasospasm, the fibrous cap can become disrupted, exposing the contents of the plaque to the flowing blood. The resulting thrombus can lead to ischemia or to the shedding of emboli.

One method of locating vulnerable plaque is to peer through the arterial wall with infrared light. To do so, one inserts a catheter through the lumen of the artery. The catheter includes a delivery fiber for illuminating a spot on the arterial wall with infrared light. Various particles in the blood, as well as the arterial wall itself, scatter or reflect much of this light. A small portion of the light, however, penetrates the arterial wall, scatters off structures deep within the wall. Some of this deeply-scattered light re-enters the lumen. This re-entrant light be collected by a collection fiber within the catheter and subjected to spectroscopic analysis.

Light scattered only by the blood or reflected off the vessel walls surface contains no information about structures within the wall. To the extent that such light enters the collection fiber, it represents unwanted noise. Hence, the collection fiber preferably rejects such light and directs only re-entrant light into the collection fiber.

SUMMARY

The invention is based on the recognition that one can use the differing spatial distributions of specularly reflected light and re-entrant light to preferentially guide re-entrant light into the collection fiber.

In one aspect, the invention includes a spectroscope having an optical fiber extending through a catheter. An obstruction is placed so as to occlude a portion of a field-of-view of the optical fiber.

A variety of obstructions are within the scope of the invention. For example, in some embodiments, the obstruction includes a ledge extending across a chord of fiber core so as to occlude a region bounded by the chord and by a boundary of the core. In other embodiments, the obstruction includes a tab extending at least part way across the core. In yet other embodiments, the obstruction includes a disk disposed to occlude a circular portion of the core.

The obstruction need not be adjacent to the fiber. For example, in spectroscopes that include a mirror in optical communication with the optical fiber, the obstruction can be a non-reflective region of the mirror shaped to obstruct a portion of the fibers field-of-view. Or, for spectroscopes that include a perforated mask enclosing the fiber, the obstruction can be walls forming an aperture in optical communication with the fiber, the aperture being shaped to obstruct a portion of the fibers field-of-view. For spectroscopes that include a transparent sheath surrounding the fiber, the obstruction can be an opaque band in optical communication with the fiber and positioned to obstruct a portion of the fibers field-of-view.

The resulting field of view of the optical fiber depends in part on the shape of the obstruction. In some embodiments, the obstruction has a shape selected to form a field-of-view in the shape of a truncated ellipse. This includes the special case of a truncated circle, a circle being an ellipse with coincident foci. In other embodiments, the obstruction has a shape selected to form a crescent-shaped field-of-view. In yet other embodiments, the obstruction has a shape selected to form an annular field-of-view. Additional embodiments include those in which the obstruction has a diffracting edge, the geometry of which is selected to form a selected field-of-view.

Another aspect of the invention includes a spectroscope having an optical fiber that extends through a catheter. An optical system having a finite focal length is disposed to be in optical communication with the fiber.

In some embodiments, the optical system includes an optical element having a curved surface. Examples of such optical elements include mirrors and lenses. The curved surface can be a cylindrical surface, or it can be a paraboloid, an ellipsoid, a hyperboloid, or a sphere. In other embodiments, the optical system includes an optical element with a spatially varying index of refraction.

Another aspect of the invention includes a spectroscope having a catheter and an optical fiber extending through the catheter. In this aspect, a diffracting element configured to form a selected field-of-view is in optical communication with the fiber.

Embodiments of the spectroscope include those in which the diffracting element is a transmissive diffracting element and those in which the diffracting element is reflective diffracting element. Other embodiments include those in which the diffracting element is a diffraction grating, an amplitude grating, a phase grating, or a holographic grating.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

System Overview

Figure 1:
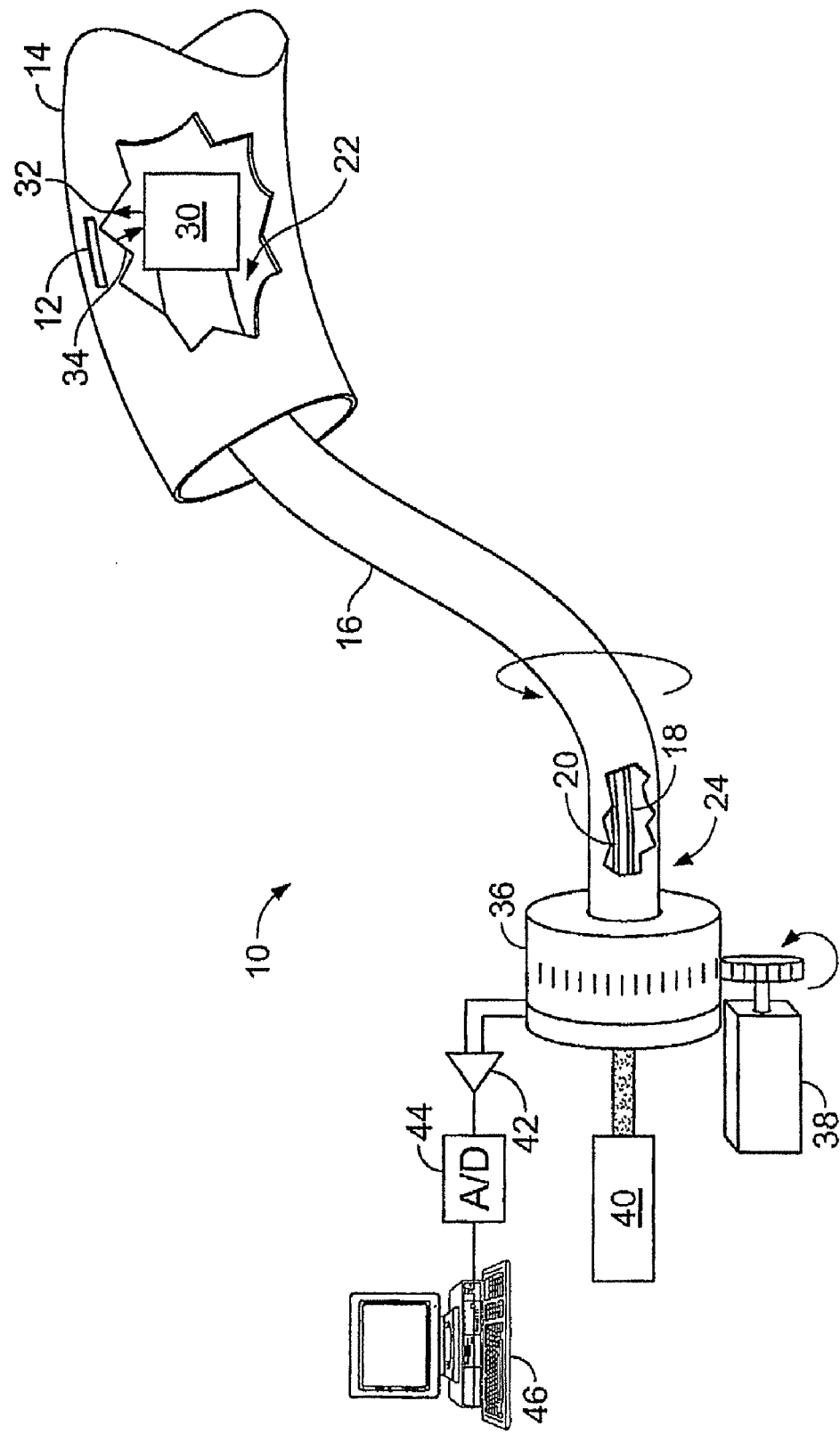
FIG. 1 is a schematic of a system for identifying vulnerable plaque in a patient.

FIG. 1 shows a diagnostic system 10 for identifying vulnerable plaque 12 in an arterial wall 14 of a patient. The diagnostic system features a catheter 16 to be inserted into a selected artery, e.g. a coronary artery, of the patient. A delivery fiber 18 and a collection fiber 20 extend between a distal end 22 and a proximal end 24 of the catheter 16.

Figure 2:
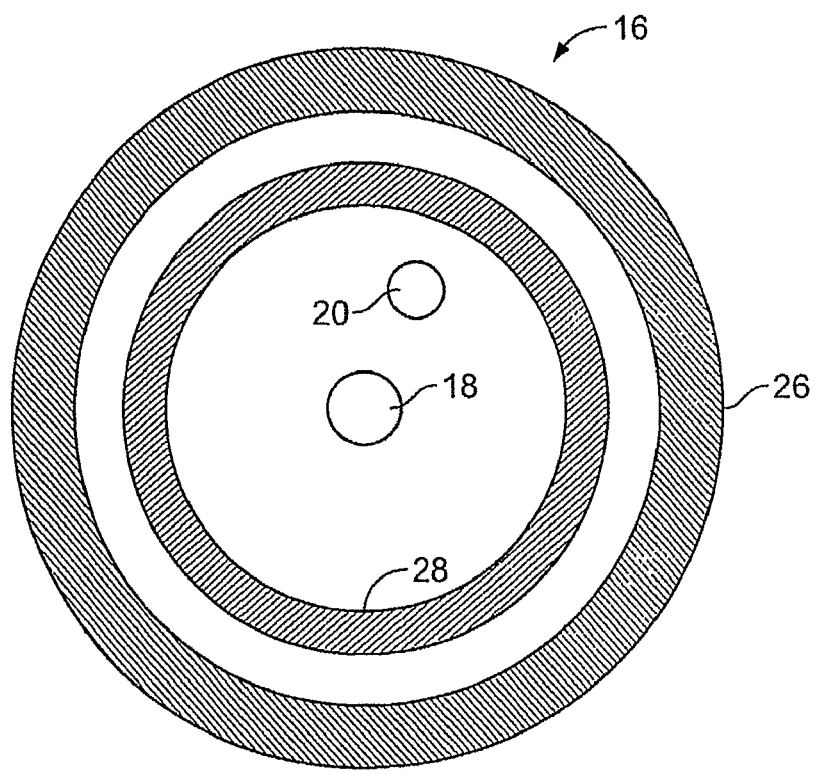
FIG. 2 is a cross-section of the catheter in FIG. 1.

As shown in FIG. 2, the catheter 16 includes a sheath 26 surrounding a rotatable torque cable 28. The delivery fiber 18 extends along the center of a torque cable 28, and the collection fiber 20 extends parallel to, but radially displaced from, the delivery fiber 18. The rotatable torque cable 28 spins at a rate between approximately 1 revolution per second and 400 revolutions per second.

At the distal end 21 of the catheter 16, a tip assembly 30 coupled to the torque cable 28 directs light traveling axially on the delivery fiber 18 toward an illumination spot 32 on the arterial wall 14. The tip assembly 30 also collects light from a field-of-view 34 on the arterial wall 14 and directs that light into the collection fiber 20.

A multi-channel coupler 36 driven by a motor 38 engages the proximal end 24 of the torque cable 28. When the motor 38 spins the multi-channel coupler 36, both the coupler 36, the torque cable 28, and the tip assembly 30 spin together as a unit. This feature enables the diagnostic system 10 to circumferentially scan the arterial wall 14 with the illumination spot 32.

In addition to spinning the torque cable 28, the multi-channel coupler 36 guides light from a laser 40 (or other light source such as a light-emitting diode, a super-luminescent diode, or an arc lamp) into the delivery fiber 18 and guides light emerging from the collection fiber 20 into one or more detectors (not visible in FIG. 1).

The detectors provide an electrical signal indicative of light intensity to an amplifier 42 connected to an analog-to-digital ("A/D") converter 44. The A/D converter 44 converts this signal into digital data that can be analyzed by a processor 46 to identify the presence of a vulnerable plaque 12 hidden beneath the arterial wall 14.

Optical Bench

Figure 3:
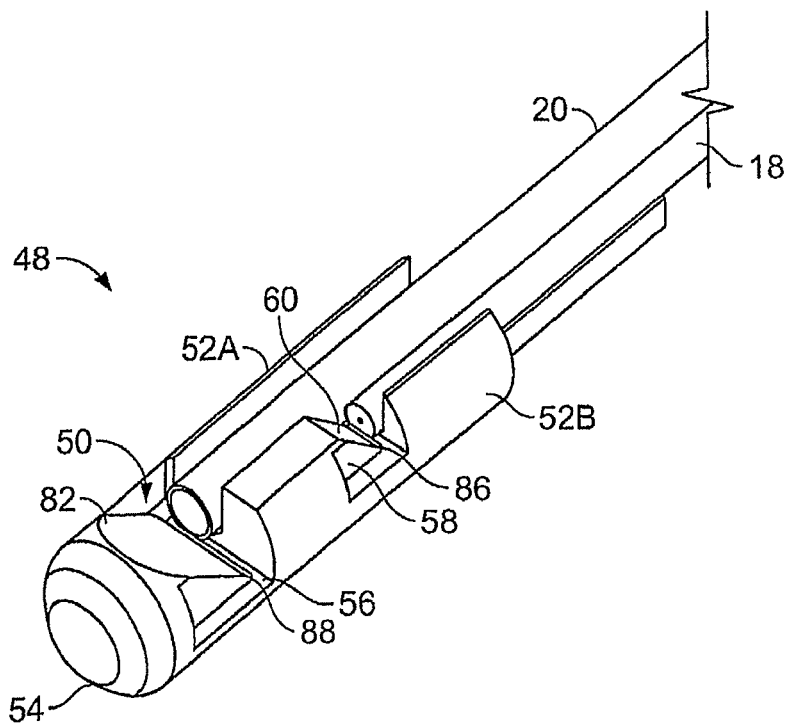
FIG. 3 is a view of an optical bench at the tip assembly of the catheter in FIG. 1.

FIG. 3 shows an optical bench 48 in which are seated the collection fiber 20 and the delivery fiber 18. The optical bench 48 is seated in a recess 50 between first and second side walls 52A-B of the distal end of a housing 54. The housing 54 is in turn coupled to the distal end of the torque cable 28. The recess 50 is just wide enough to enable the collection fiber 20 and the delivery fiber 18 to nestle adjacent to each other. A floor 56 extending between the first and second side walls 52A-B and across the recess 50 supports both the collection and delivery fibers 18, 20.

Just distal to the end of the delivery fiber 18, a portion of the optical bench 48 forms a frustum 58. The frustum 58 extends transversely only half-way across the optical bench 48, thereby enabling the collection fiber 20 to extend distally past the end of the delivery fiber 18.

The frustum 58 has an inclined surface facing the distal end of the delivery fiber 18 and a vertical surface facing the distal end of the optical bench 48. The inclined surface forms a 135 degree angle relative to the floor 56. Other angles can be selected depending on the direction in which light from the delivery fiber 18 is to be directed. A reflective material coating the inclined surface forms a beam re-director, which in this case is a delivery mirror 60. When light exits axially from the delivery fiber 18, the delivery mirror 60 intercepts that light and redirects it radially outward to the arterial wall 14. Examples of other beam re-directors include prisms and diffraction gratings.

Spatial Distribution of Light

Figure 4:
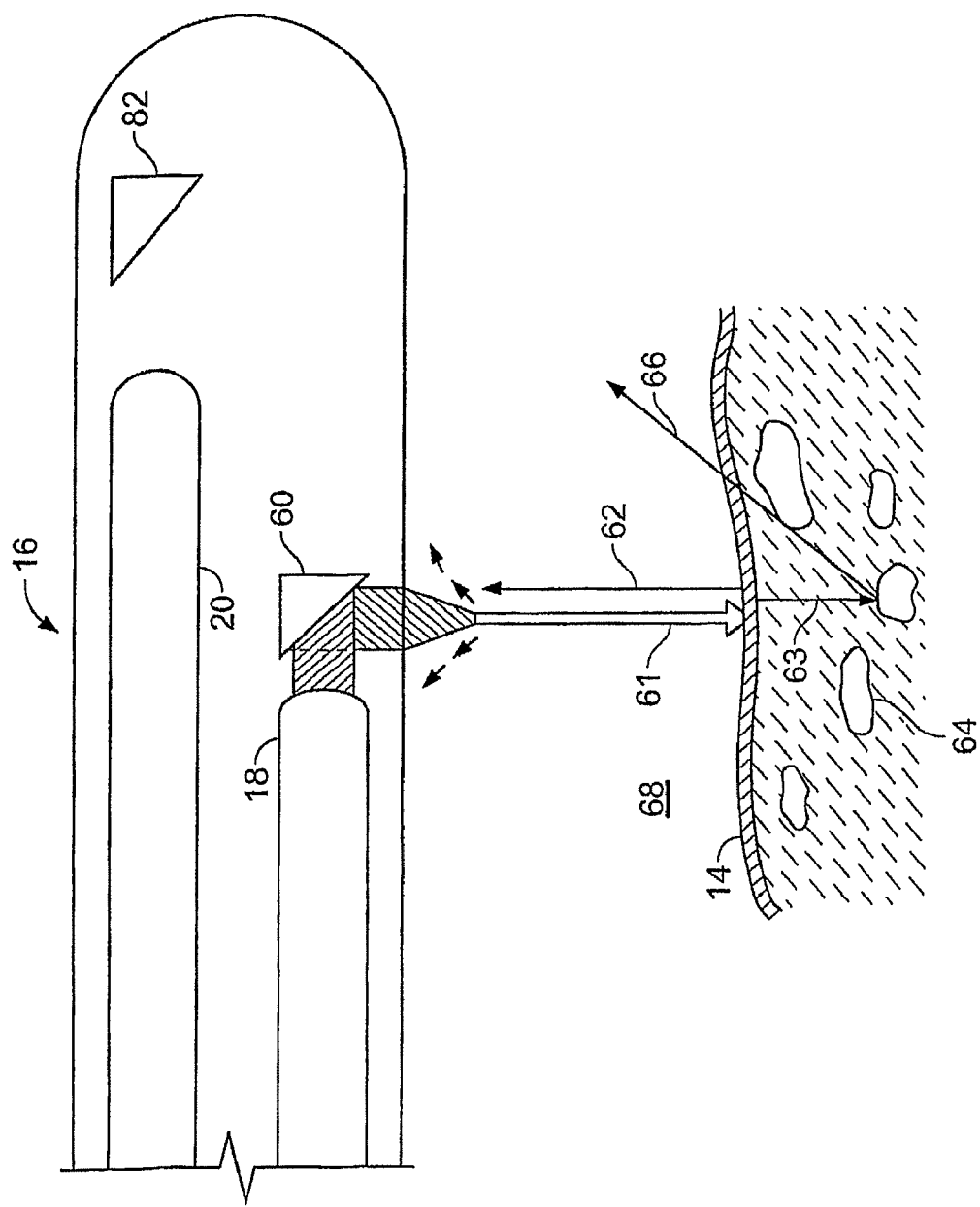
FIG. 4 is a schematic of the paths traveled by light from the illumination fiber of FIG. 1.

Referring to FIG. 4, as the light travels radially outward from the delivery mirror 60, it encounters the blood that fills a lumen 68. As a result of scattering by particles in the blood, a large number of photons never reach the wall 14. This loss of energy is shown schematically by a progressive narrowing of the beam as it nears the wall 14. The remaining photons 61 eventually reach the arterial wall 14. Some of these photons are reflected from the wall 14. These specularly reflected photons 62 carry little or no information about structures 64 behind the arterial wall 14 and are therefore of little value. Of those photons 63 that penetrate the wall, many are absorbed. The remainder 66 are scattered by structures 64 behind the wall 14. After having been scattered, a few of these remaining photons 66 again pass through the arterial wall 14 and re-enter the lumen 68. This remnant of the light 61 originally incident on the wall, which is referred to herein as the "re-entrant light 66," carries considerable information about the structures 64 behind the arterial wall 14. It is therefore this re-entrant light 66 that is to be guided into the collection fiber 20.

Figure 5:
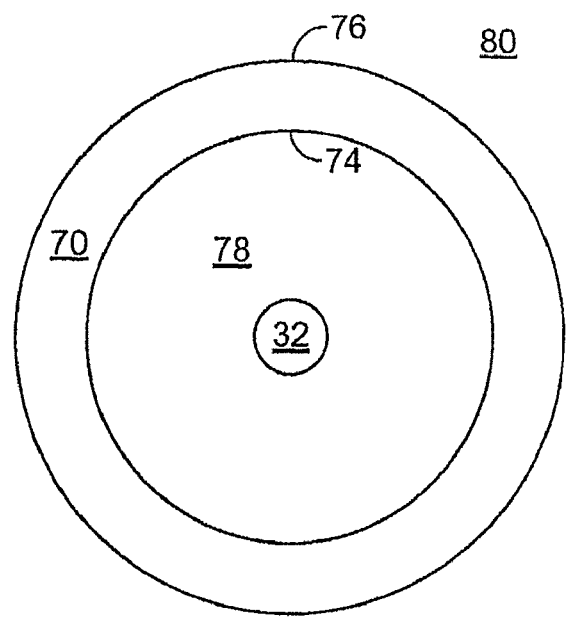
FIG. 5 is a cross-section of the spatial light distribution shown in FIG. 4.

As suggested by FIG. 4, re-entrant light 66 tends to re-enter the lumen along an annular re-entrant zone that is radially separated from the specularly reflected light 62. FIG. 5, which illustrates the spatial distribution of light from the viewpoint of the catheter 16, shows such a re-entrant zone 70 surrounding an illumination spot 32. Photons received from within the re-entrant zone 70 are predominantly those that have been scattered from within the arterial wall 14. The re-entrant zone 70 has an inner circumference 74 and an outer circumference 76. Between the inner circumference 74 and the illumination spot 32 lies a specular zone 78. Photons received from the specular zone 78 are predominantly those that have undergone specular reflection. Proceeding radially outward beyond the outer circumference 76, one comes to a dark zone 80, where the number of photons of either type is so small as to be immeasurable.

Modifying the Field-of-View

To collect as many photons of re-entrant light 66 as possible, the field-of-view 32 should overlap the re-entrant zone 70 to the greatest extent possible. To the extent that the field-of-view 32 extends outside the re-entrant zone 70, it should extend into the dark zone 80 and away from the specular zone 78.

Modifying the Field-of-View with an Obstruction

Referring back to FIG. 3, the collection fiber 20 extends past the end of the delivery fiber 18 until it terminates at a plane that is coplanar with the vertical face of the frustum 58. Just beyond the distal end of the collection fiber 20, a portion of the optical bench 48 forms an inclined surface extending transversely across the optical bench 48 and making a 135 degree angle relative to the floor 56. A reflective material coating the inclined surface forms a collection mirror 82. This collection mirror 82 reflects light incident from the arterial wall 14 into the distal end of the collection fiber 20. The collection mirror 82 and the collection fiber 20 together form a collection subsystem 84 that collects light from a field-of-view 32.

A delivery-fiber stop 86 molded into the optical bench 48 proximal to the frustum 58 facilitates placement of the delivery fiber 18 at a desired location proximal to the delivery mirror 60. Similarly, a collection-fiber stop 88 molded into the optical bench 48 just proximal to the collection mirror 82 facilitates placement of the collection fiber 20 at a desired location proximal to the collection mirror 82.

Figure 6:
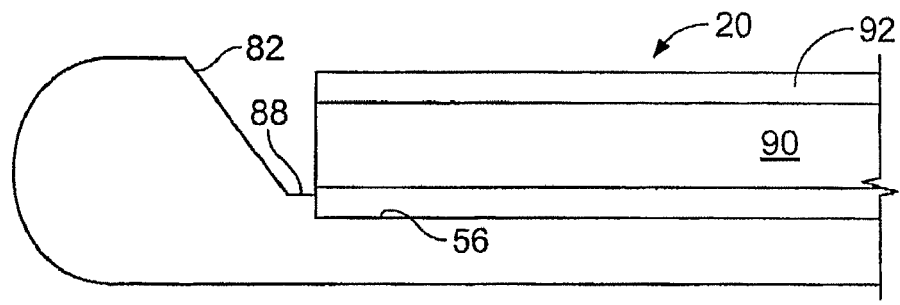
FIG. 6 is a transverse cut of the collection fiber and optical bench showing a known collection-fiber stop.

Referring now to FIG. 6, the collection fiber has an optically transmissive core 90 surrounded by a protective cladding 92. The collection-fiber stop 88 extends upward from the floor 56 to provide an abutment surface for the collection fiber 20. A portion of the cladding 92 rests on the abutment surface. The core 90 does not rest on the abutment surface and therefore remains unobstructed.

Figure 7:
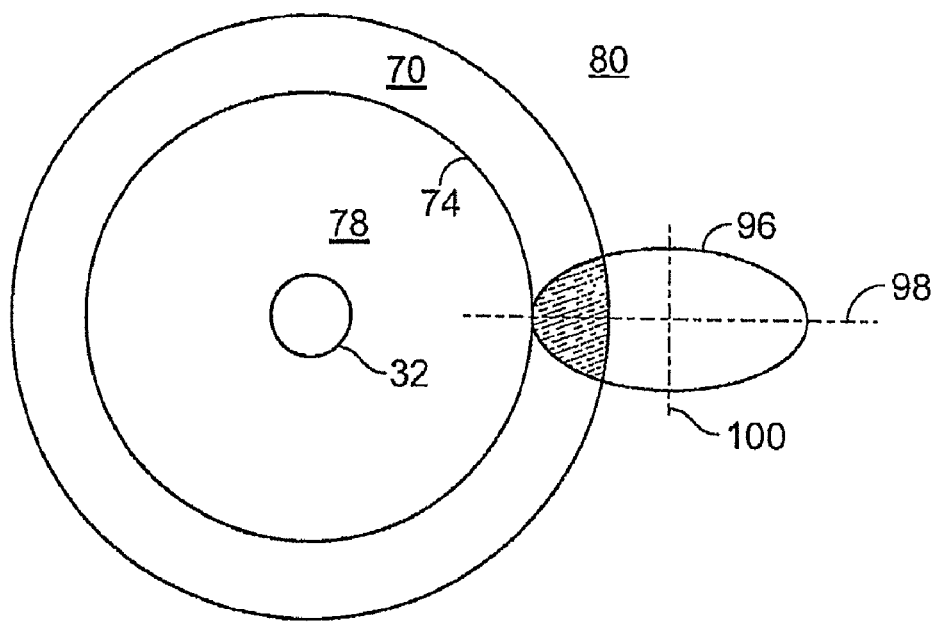
FIG. 7 is a schematic of the field-of-view of the collection fiber of FIG. 6 superimposed on the spatial light distribution of FIG. 4.

A distal tip assembly 94 configured as shown in FIG. 6 results in a field-of-view 32 shaped like an ellipse 96 with its major axis 98 extending along the radial direction, as shown in FIG. 7. The extent to which the ellipse 96 overlaps the re-entrant zone 70 is one measure of how effective the collection subsystem 84 is at guiding re-entrant light into the collection fiber 20.

The extent of the overlap between the ellipse 96 and the re-entrant zone 70 depends on the eccentricity of the ellipse and its position relative to the re-entrant zone 70. The eccentricity of the ellipse 96 is governed by the angular orientation of the collection mirror 82. Its position relative to the re-entrant zone 70 is controlled by varying the position and angle of the delivery mirror 60 relative to the collection mirror 82.

To avoid collecting photons from the specular zone 78, the ellipse 96 is positioned to be tangent to the inner circumference 74 of the re-entrant zone 70, with its minor axis 100 located radially outward from the point of tangency.

Figure 8:
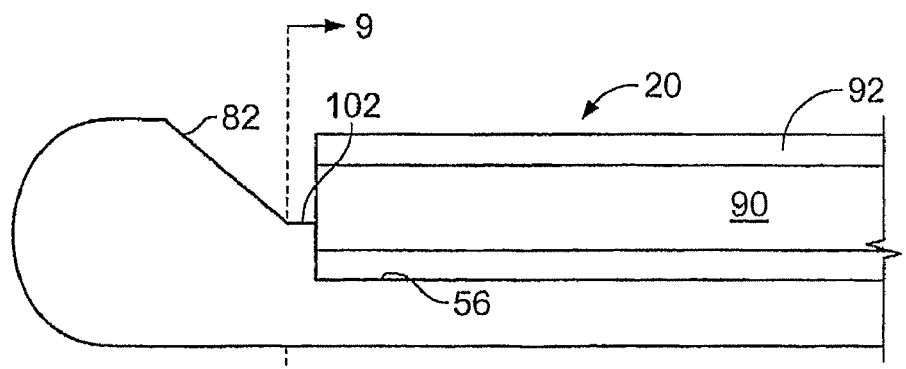
FIGS. 8 and 9 are longitudinal and transverse cross-sections of an optical bench having an extended collection-fiber stop.
Figure 10:
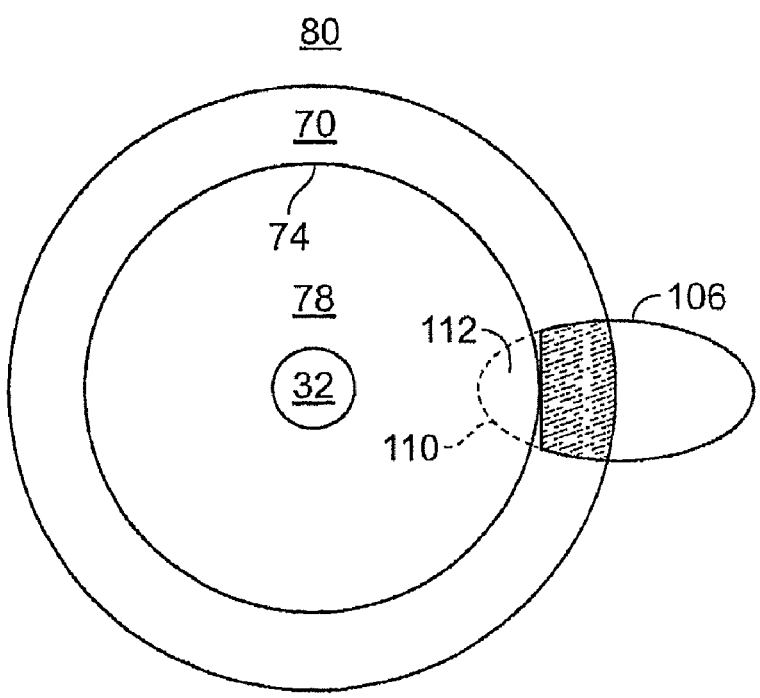
FIG. 10 is a schematic of a field-of-view of resulting from the extended collection-fiber stop of FIGS. 8 and 9.
Figure 9:
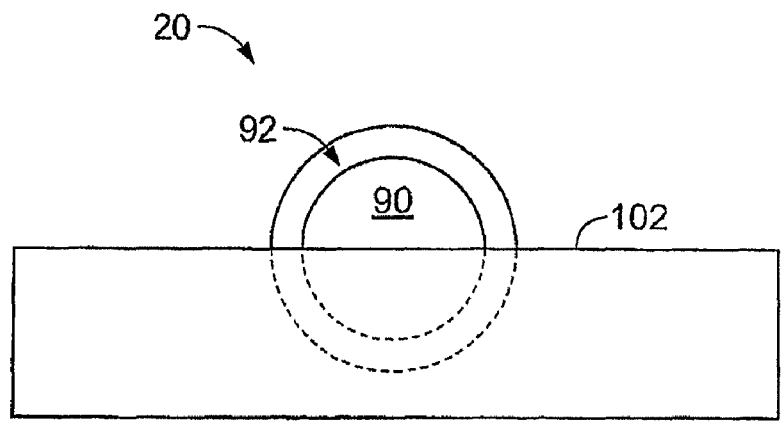

FIGS. 8 and 9 show an extended collection-fiber stop 102 forms an abutment surface that extends part-way across the core 90 of the collection fiber. The occluded portion of the core 90 is bounded by a chord extending across the core 90 and by an arc that forms part of the boundary between the core 90 and the cladding 92. The resulting modified field-of-view is a truncated ellipse 106 having a base 108, as shown in FIG. 10. A dotted line 110 outlines a portion 112 of the ellipse truncated by the extended collection-fiber stop 102. To avoid collecting photons from the specular zone 78, the truncated ellipse 106 is positioned such that the base 108 of the truncated ellipse 106 is tangent to the inner circumference 74 of the re-entrant zone 70.

The overlap between the truncated ellipse 106 and the re-entrant zone 70 in FIG. 10 is greater than the overlap between the full ellipse 96 and the re-entrant zone 70 in FIG. 7. The extent to which these overlaps differ represents an increase in the number of photons gathered from the re-entrant zone 70.

Figure 11:
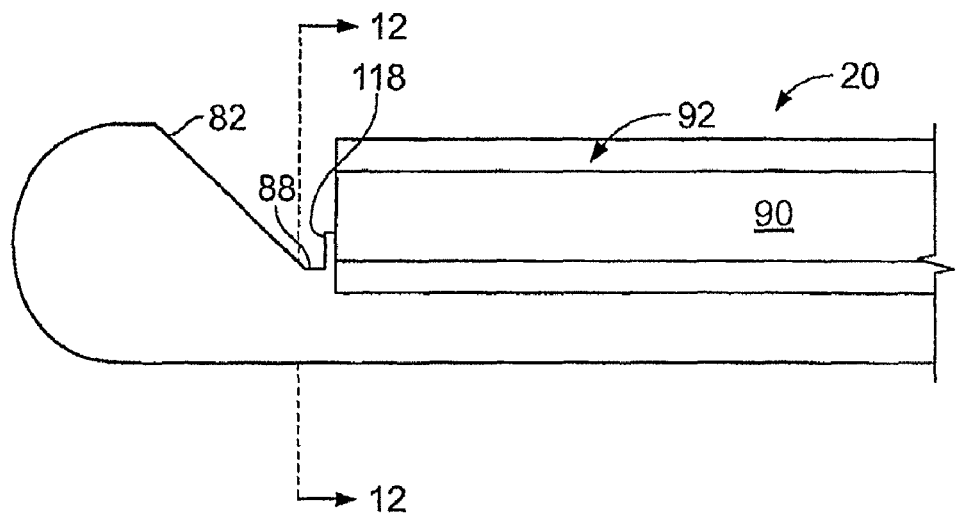
FIGS. 11 and 12 are longitudinal and transverse cross-sections of an optical bench having a tab protruding from the collection-fiber stop.
Figure 12:
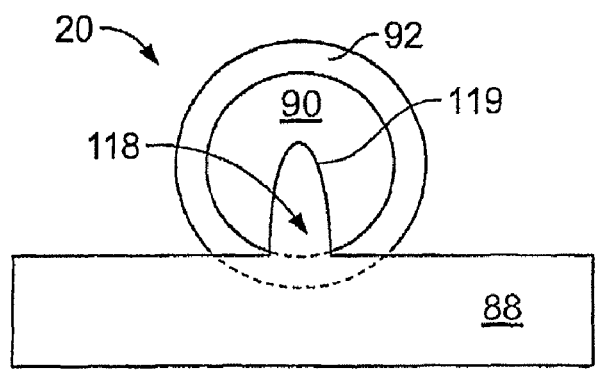
Figure 13:
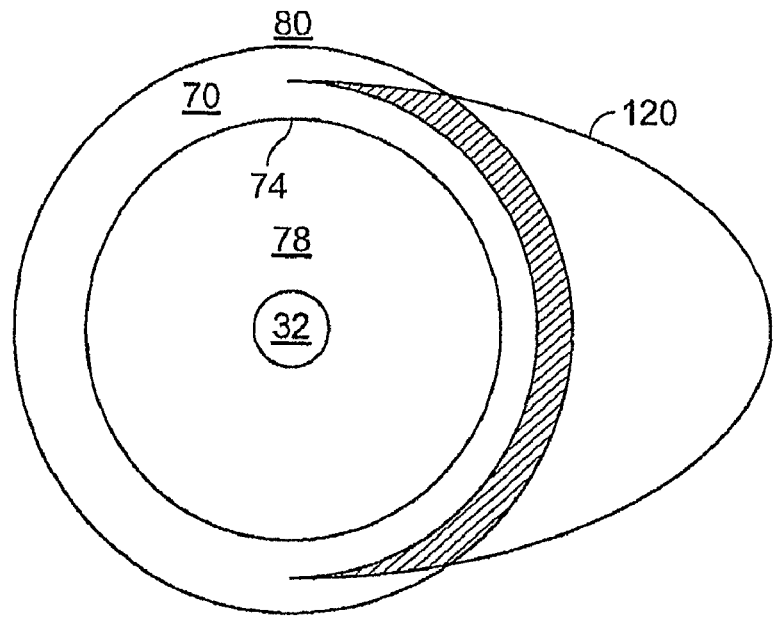
FIG. 13 is a schematic of a crescent-shaped field of view resulting from the tab of FIGS. 11 and 12.

Other beam-shaping structures can be used to prevent light from illuminating the entire core 90 and to thereby shape the field-of-view 32. In FIGS. 11 and 12, for example, a tab 118 having a curved distal tip 119 protrudes vertically upward from the collection-fiber stop 88 and obstructs part of the core 90. When placed in front of a collection fiber 20 having a suitably high numerical aperture, this results in a crescent shaped field-of-view 120 as shown in FIG. 13.

Figure 14:
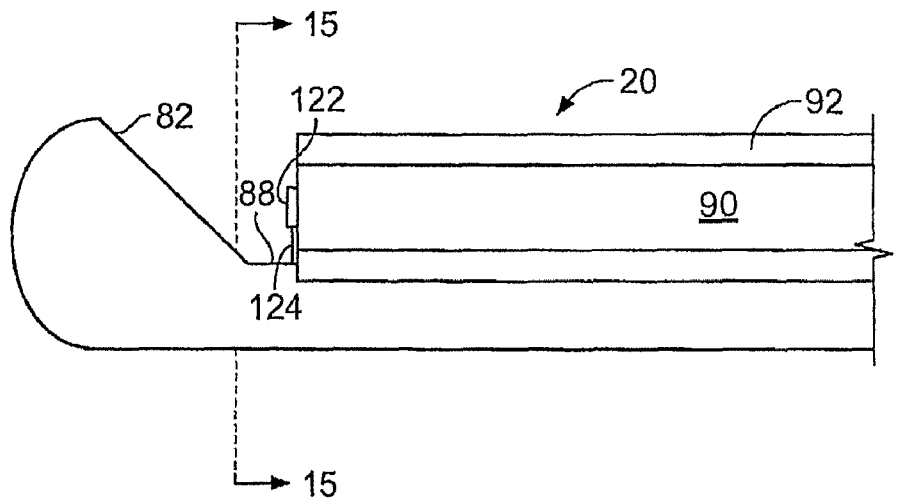
FIGS. 14 and 15 are longitudinal and transverse cross-sections of an optical bench having an occluding disk supported on a post protruding from the collection-fiber stop.
Figure 15:
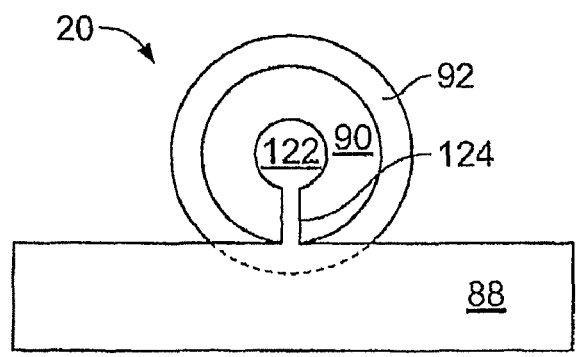

Another example, shown in FIGS. 14 and 15, is an occulting disk 122 mounted on a post 124 that protrudes from the collection-fiber stop 88. The post 124 supports the occulting disk 122 so that its center coincides with the center of the core 90. The diameter of the occulting disk 122 is slightly smaller than the diameter of the core 90. The difference between the diameter of the occulting disk 122 and that of the core 90 is selected to provide an annular field-of-view that closely matches the size and shape of the re-entrant zone 70.

Figure 16:
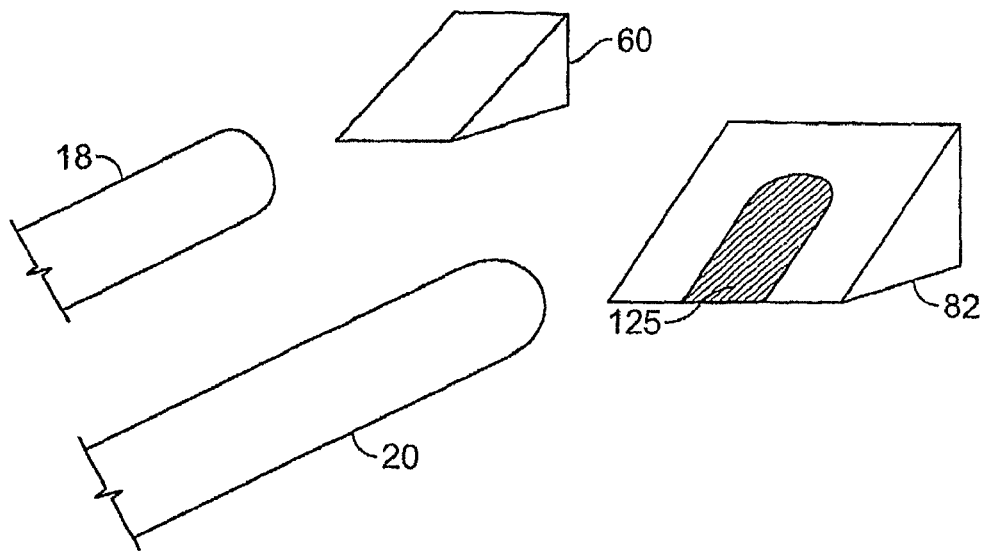
FIG. 16 is a plan view of a mask on the collection mirror.
Figure 17:
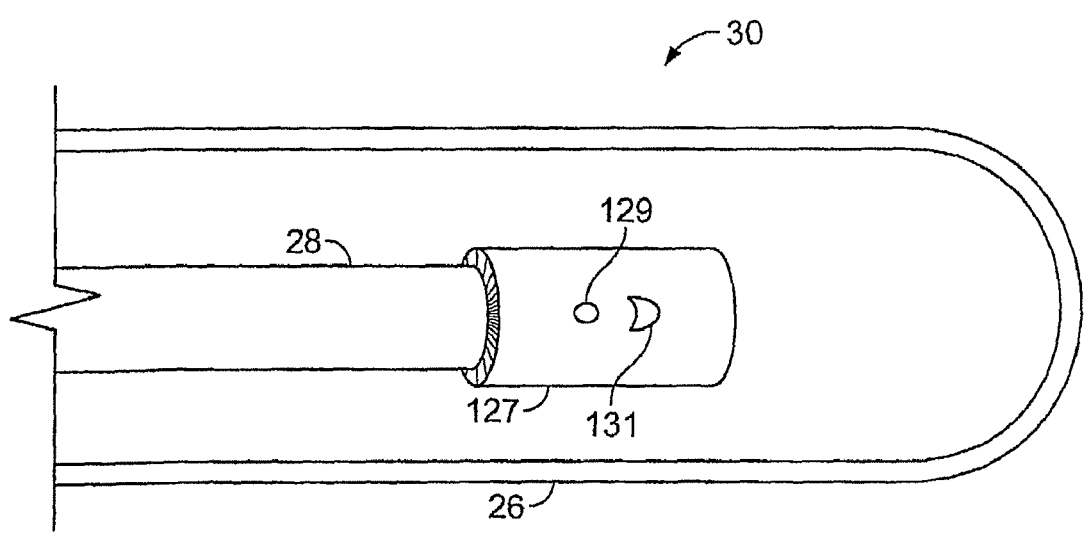
FIG. 17 is a schematic of a perforated shell enclosing the distal tip assembly.
Figure 18:
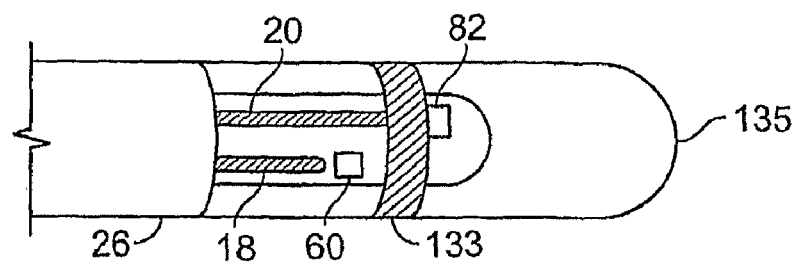
FIG. 18 is a schematic of a banded sheath enclosing the distal tip assembly.

Structures that effectively block light from entering a portion of the collection fiber need not be adjacent to the collection fiber 20, as shown in FIGS. 11-12 and in FIGS. 14-15. In fact, such structures can be placed anywhere along the optical path between the collection fiber 20 and the arterial wall 14. For example, a beam-shaping structure that effectively obstructs a portion of the core 90 can be a mask 125 formed directly on the collection mirror 82, as shown in FIG. 16. Another example of such a structure is a perforated shell 127 rotationally coupled to the torque cable 28, as shown in FIG. 17. The perforated shell 127 has a delivery aperture 129 to permit light from the delivery fiber 18 to pass through the shell 127 unimpeded, and a collection aperture 131 shaped to block a portion of the light incident on the collection mirror 82. In another example, shown in FIG. 18, an opaque band 133 on a transparent distal tip 135 of the stationary sheath 26 is positioned to obscure a portion of the collection mirror 82. The band 131 extends circumferentially around the sheath so that the collection mirror 82 is obscured as the torque cable 28 rotates the collection mirror 82.

Any of the foregoing beam-shaping structures can have an edge that is modified to diffract light incident thereon in a manner that causes the field-of-view to have a pre-selected geometry. Such an edge can be formed by providing protrusions or indentations having a dimension on the order of the wavelength of light to be observed.

Modifying the Field-of-View with an Optical System

Figure 19:
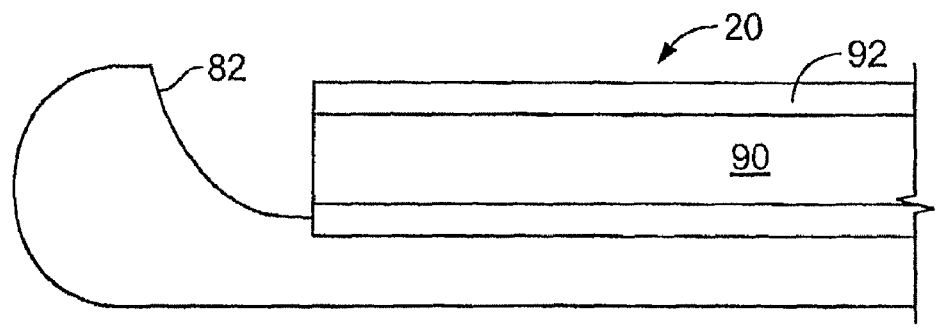
FIG. 19 is a schematic of a mirror having a curved surface in optical communication with the collection fiber.
Figure 20:
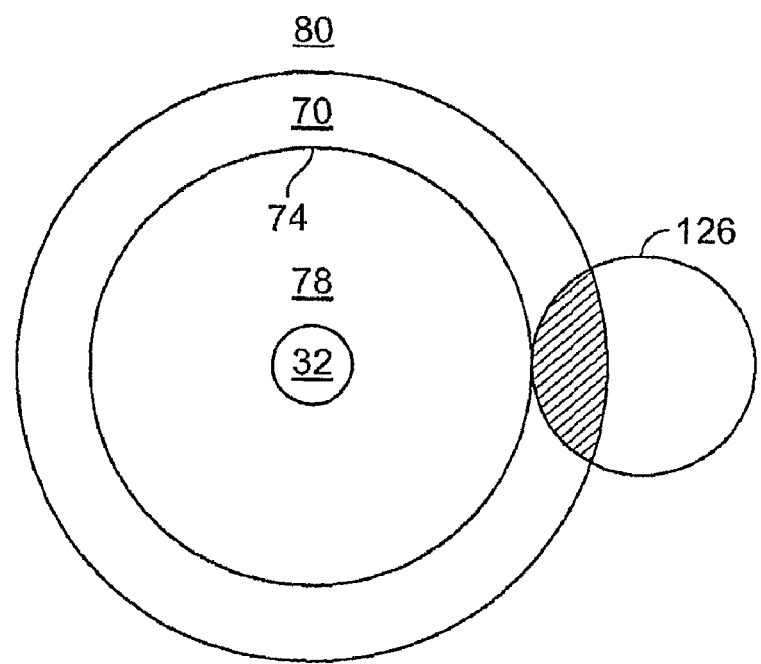
FIGS. 20 and 21 are schematics of exemplary fields-of-view as modified by mirrors having various curved surfaces.
Figure 21:
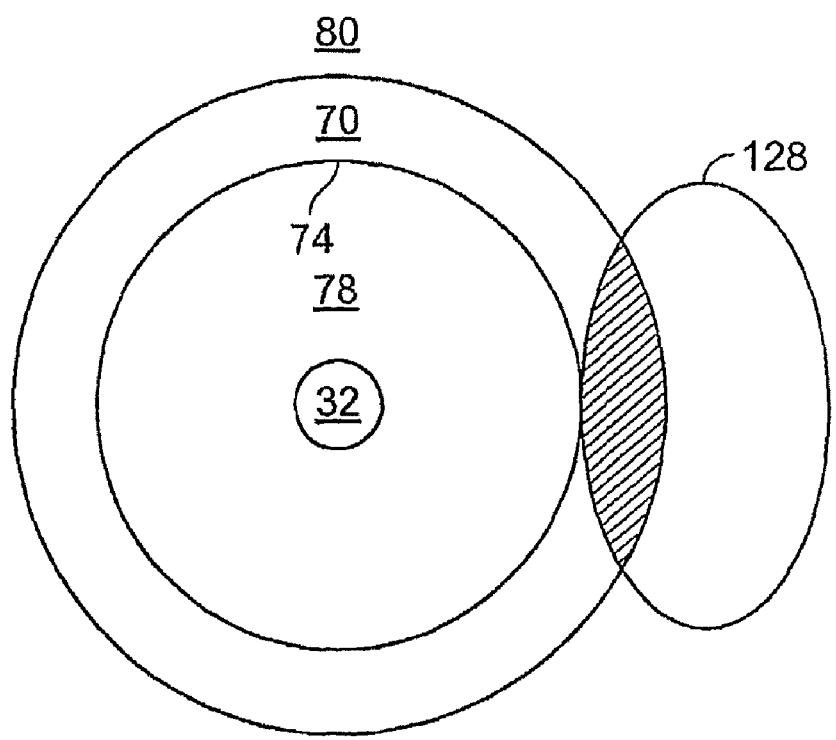

The beam-shaping function of the foregoing obstructions can also be achieved by providing an optical system in optical communication with the collection mirror 82. Such an optical system can include a collection mirror 82 with a curved surface, a lens assembly, or both. For example, in FIG. 19, the collection mirror 82 has a cylindrical surface rather than a planar surface. The resulting field-of-view for the configuration shown in FIG. 19 is an ellipse 126 having an aspect ratio closer to unity, as shown in FIG. 20. Other curved surfaces can result in fields-of-view or alternatively an ellipse 128 in which it is the minor axis of an ellipse 128, rather than the major axis, that extends radially, as shown in FIG. 21.

Curved surfaces other than a cylindrical surface can also be used to shape the field-of-view to more closely approximate the shape of the re-entrant zone 70. For example, the curved surface can be a conic surface, such as a paraboloid, a hyperboloid, or an ellipsoid. Alternatively, the surface can be a spherical surface.

Optical elements other than reflecting surfaces can also be used to shape the field-of-view. For example, in FIG. 22, a lens assembly 130 disposed in optical communication with the collection fiber 20 provides control over the shape of the field-of-view.

Figure 22:
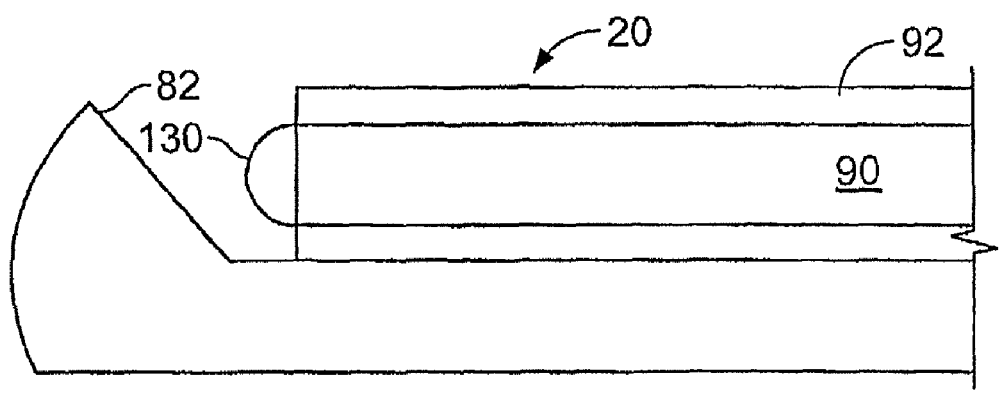
FIG. 22 is a schematic of a lens in optical communication with the collection fiber.

The lens assembly 130 can include one or more discrete lenses. One or more lenses in the lens assembly can have a suitably curved surface. Another lens suitable for use in a lens assembly is a GRIN (graduated index of refraction) lens having a spatially varying index of refraction. In addition, the lens assembly 130 need not be composed of discrete lenses but can instead include a lens that is integral with the distal end of the collection fiber 20. Such a lens 132, an example of which is shown in FIG. 22, can be made by shaping the distal end of the collection fiber 20 so that it has the desired optical characteristics.

Figure 23:
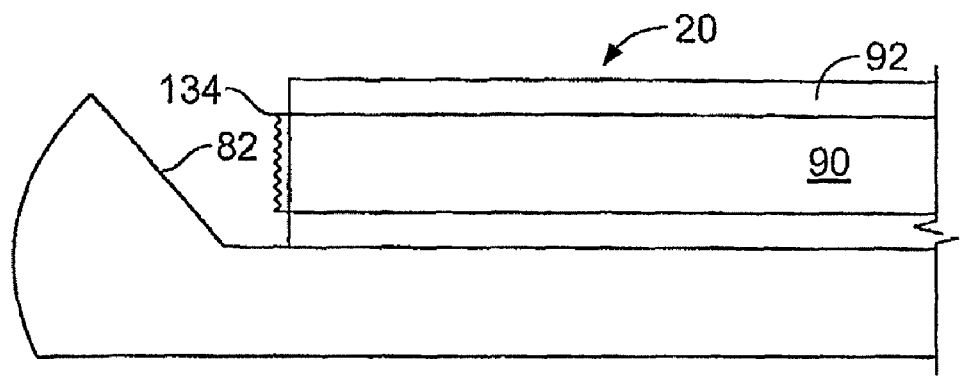
FIG. 23 is a schematic of a transmissive diffracting element in optical communication with the collection fiber.
Figure 24:
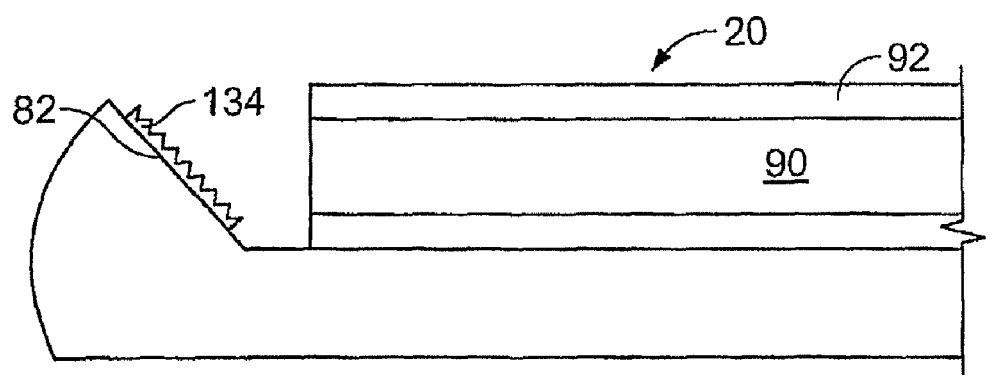
FIG. 24 is a schematic of a reflective diffractive element integrated onto the surface of the collection mirror.

The beam-shaping function provided by the foregoing examples of optical systems can also be provided by a diffracting element 134 placed along the optical path, as shown in FIG. 23. Examples of diffracting elements 134 include diffraction gratings, amplitude gratings, spatial light modulators, and holographic gratings. The diffracting element can be a transmissive or reflective. A transmissive diffracting element 134 can be placed anywhere along the optical path traversed by the collection beam, either integrated onto the distal end of the collection fiber 20, as shown in FIG. 23, or mounted separately on the optical path, either between the collection fiber 20 and the mirror 82 as shown in FIG. 23, or between the collection mirror 82 and the arterial wall. A reflective diffracting element 134 can be integrated directly onto the surface of the collection mirror 82 as shown in FIG. 24.

The surfaces of the delivery and collection mirrors 60, 82 can be coated with a reflective coating, such as gold, silver or aluminum. These coatings can be applied by known vapor deposition techniques. Alternatively, for certain types of plastic, a reflective coating can be electroplated onto those surfaces. Or, the plastic itself can have a reflective filler, such as gold or aluminum powder, incorporated within it.

The optical bench 48 is manufactured by injection molding a plastic into a mold. In addition to being simple and inexpensive, the injection molding process makes it easy to integrate the elements of the optical bench 48 into a single monolith and to fashion structures having curved surfaces. Examples of suitable plastics include liquid crystal polymers (LCPs), polyphenylsulfone, polycarbonate, acrylonitrile butadiene-styrene ("ABS"), polyamide ("NYLON"), polyethersulfone, and polyetherimide. Alternatively, the optical bench can be manufactured by micro-machining plastic or metal, by lithographic methods, by etching, by silicon optical bench fabrication techniques, or by injection molding metal. Materials other than plastics can be used to manufacture the housing 54 and the optical bench 48. Such materials include metals, quartz or glass, and ceramics.

The floor 56 in the illustrated embodiment is integral to the housing 54. However, the floor 56 can also be made part of the optical bench 48.

As described herein, the housing 54 and the optical bench 48 are manufactured separately and later joined. However, the housing 54 and the optical bench 48 can also be manufactured together as a single unitary structure.

Using the Catheter

In use, the distal tip assembly 94 is inserted into a blood vessel, typically an artery, and guided to a location of interest. Light is then directed into the delivery fiber 18. This light exits the delivery fiber 18 at its distal tip, reflects off the delivery mirror 60 in a direction away from the plane containing the delivery and collection fibers 18, 20, and illuminates an illumination spot 32 on the wall of the artery. Light penetrating the arterial wall 14 is then scattered by structures within the wall. Some of this scattered light re-enters the blood vessel and impinges on the plane and onto the collection mirror 82. The collection mirror 82 directs this light into the collection fiber 20.

Alternatively, light incident on the wall 14 can stimulate fluorescence from structures on or within the wall 14. The portion of this fluorescent light that is incident on the collection mirror 82 is directed into the collection fiber 20.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A spectroscope for spectroscopic analysis of a sample of tissue within a blood vessel wall, the spectroscope comprising:
a catheter;
a first optical fiber extending through the catheter;
a second optical fiber extending through the catheter;
a first optical system in optical communication with the first optical fiber for directing light form the first optical fiber to the illumination spot on the wall of a blood vessel; and
a second optical system including at least one optical element with a finite focal length in optical communication with the second optical fiber,
wherein the second optical system is configured to modify a field of view of the second optical fiber so that the modified field of view overlaps an annular re-entrant zone radially separated from the illumination spot by a specular zone predominantly made up of light specularly reflected from the wall, while avoiding the specular zone.

2. The spectroscope of claim 1, wherein the at least one optical element has a curved surface.

3. The spectroscope of claim 2, wherein the curved surface comprises a cylindrical surface.

4. The spectroscope of claim 2, wherein the curved surface includes a parabolic surface.

5. The spectroscope of claim 2, wherein the curved surface includes a ellipsoidal surface.

6. The spectroscope of claim 2, wherein the curved surface includes a hyperbolic surface.

7. The spectroscope of claim 2, wherein the curved surface includes a spherical surface.

8. The spectroscope of claim 1, wherein the at least one optical element has a spatially varying index of refraction.

9. The spectroscope of claim 1, wherein the at least one optical element is a mirror having a curved surface.

10. The spectroscope of claim 1, wherein the at least one optical element is a lens.

11. The spectroscope of claim 10, wherein the lens is integral with a distal end of the second optical fiber.

12. The spectroscope of claim 1 wherein the at least one optical element is
a diffracting element.

13. The spectroscope of claim 12, wherein the diffracting element comprises a transmissive diffracting element.

14. The spectroscope of claim 12, wherein the diffracting element comprises a reflective diffracting element.

15. The spectroscope of claim 12, wherein the diffracting element comprises a diffraction grating.

16. The spectroscope of claim 12, wherein the diffracting element comprises an amplitude grating.

17. The spectroscope of claim 12, wherein the diffracting element comprises a phase grating.

18. The spectroscope of claim 12, wherein the diffracting element comprises a holographic grating.

19. The spectroscope of claim 1, wherein the at least one optical element is a reflecting element having a curved reflective surface.

20. The spectroscope of claim 1, wherein the second optical system is configured to modify a shape of the field of view of the second optical fiber.

21. The spectroscope of claim 1, wherein the modified field of view is substantially ellipse-shaped.

22. The spectroscope of claim 21, wherein a minor axis of the ellipse-shaped field of view extends radially relative to a center of the specular zone.

23. The spectroscope of claim 21 wherein the ellipse-shaped field of view has an aspect ratio of about unity.

24. The spectroscope of claim 1 wherein the first and second optical systems are configured to redirect the respective fields of view of the first and second optical fibers.

25. A method for spectroscopic analysis of a sample of tissue within a blood vessel wall, the method comprising:
inserting a catheter into the blood vessel, the catheter having first and second optical fibers extending therethrough, a first optical system in optical communication with the first optical fiber, and a second optical system in optical communication with the second optical fiber, the second optical system including at least one optical element with a finite focal length in optical communication with the second optical fiber;
directing light from the first optical fiber to an illumination spot on the wall of the blood vessel;
using the second optical system to modify a field of view of the second optical fiber so that the modified field of view overlaps an annular re-entrant zone radially separated from the illumination spot by a specular zone predominantly made up of light specularly reflected from the wall, while avoiding the specular zone;
collecting light within the modified field of view of the second optical system and transmitting it via the second optical fiber; and
analyzing the transmitted light.

26. The method of claim 25 wherein using the second optical system to modify the field of view of the second optical fiber includes changing a shape of the field of view of the second optical fiber.

27. The method of claim 25 wherein the second optical system is configured such that the modified field of view is ellipse-shaped.

28. The method of claim 27 wherein the second optical system is configured such that a minor axis of the ellipse-shaped field of view extends radially relative to a center of the specular zone.

29. The method of claim 25 further comprising the step of using the second optical system to redirect the field of view of the second optical fiber.

* * * * *